United States Patent [19]

Childers

[11] Patent Number: 5,068,087

[45] Date of Patent: Nov. 26, 1991

[54] HIGH CAPACITY MULTICOMPONENT LIQUID VAPORIZER

[75] Inventor: Robert W. Childers, Erie, Pa.

[73] Assignee: American Sterilizer Company, Erie, Pa.

[21] Appl. No.: 292,271

[22] Filed: Dec. 30, 1988

[51] Int. Cl.⁵ .............................. A61L 2/20; F22B 3/00
[52] U.S. Cl. ........................................ 422/26; 122/4 A;
    159/408; 422/28; 422/298; 422/299
[58] Field of Search .................. 422/26, 28, 298, 299,
    422/1; 122/4 A; 159/4.08

[56] References Cited

U.S. PATENT DOCUMENTS 3,836,328  9/1974  Beauvais et al. ............... 422/26 X
3,988,112 10/1976  Johansson et al. ............ 422/26 X
4,424,189  1/1984  Hick .............................. 422/298 X Primary Examiner—Jill Johnston
Attorney, Agent, or Firm—Kirkpatrick & Lockhart

[57] ABSTRACT

An apparatus for vaporizing a multicomponent liquid consists of a vaporization chamber into which liquid is injected through a nozzle with sufficient velocity to ensure multiple impingements with the heated surfaces of the chamber so that vaporization is substantially complete. The apparatus may have a plurality of injection nozzles, each responsive to a valve. The valves are sequentially operated by a control circuit to provide a substantially continuous stream of liquid to the vaporization chamber.

16 Claims, 2 Drawing Sheets

HIGH CAPACITY MULTICOMPONENT LIQUID VAPORIZER

BACKGROUND OF THE INVENTION

1. Field of the Invention

The present invention relates to an apparatus for vaporizing liquids, and more particularly, to an apparatus for continuous vaporization of large quantities of multicomponent liquids.

2. Description of the Prior Art

In sterilization processes, items to be sterilized may be contacted with a vapor phase of a multicomponent sterilant. Such vapor phase sterilants are provided by vaporizing a liquid phase multicomponent sterilant. However, such multicomponent sterilants are often difficult to vaporize due to the difference in vaporization temperatures of the various components. If care is not exercised, preferential vaporization will occur resulting in a vapor phase of different concentration than the liquid phase which may jeopardize the efficacy of the sterilization process.

One method of vaporizing a multicomponent liquid is disclosed in U.S. Pat. No. 4,642,165 to Bier which issued on Feb. 10, 1987. In that method, a predetermined increment of the liquid is metered onto a heated surface of a vaporization chamber. Each increment is substantially instantaneously vaporized before the next increment is introduced to the surface. The vapor then passes into a vacuum chamber.

The Bier method is useful for vaporizing small quantities of liquid on the order of eight grams/minute. However, applications such as the sterilization of an entire room, require much greater quantities, on the order of one hundred and twenty grams/minute. When such large quantities of liquid are introduced into the Bier apparatus, the vaporizer loses heat faster than it can be replaced. Soon the vaporizer cannot vaporize all of the liquid, puddles form, and the vaporizer floods. A vaporizer using the Bier method is incapable of vaporizing a large continuous stream of liquid thus making it incapable of meeting large scale sterilization needs.

Another method of vaporizing a multicomponent liquid is disclosed in U.S. Pat. No. 4,424,189 to Hick which issued on Jan. 3, 1984. In that patent, a heating coil is inserted into an open-topped container. A sterilizing agent is sprayed onto the heating coil and vaporizes upon contact with the coil. Clearly, such a method which requires inserting the heating coil into the item to be sterilized is not suitable for producing a large stream of vaporized sterilant. Additionally, the heating element may act as a catalyst for degrading the vaporized sterilant. A spiral heating element such as that used in the Hick's patent presents a large surface area which exacerbates that problem.

Accordingly, there is a need for an apparatus which is capable of vaporizing large quantities of a multicomponent liquid. That is especially true for chemical sterilants, as distinguished from moist beat sterilants such as steam. The chemical vapors may not always be stable. Vapor phase hydrogen peroxide, for example, degrades into water vapor and oxygen. Thus, because current vaporizers are not capable of quickly vaporizing large quantities of liquid phase hydrogen peroxide, when a large enclosure is involved, the hydrogen peroxide vapors degrade before a desired concentration can be achieved.

SUMMARY OF THE INVENTION

The present invention provides an apparatus for vaporizing a large quantity of a multicomponent liquid. A vaporization chamber having several surfaces is heated to the vaporization temperature of the liquid to be vaporized. The chamber has an inlet for the liquid and an outlet for the vapor. The liquid is injected into the chamber at a substantial velocity to ensure multiple impingements with the heated surfaces. Following those multiple impingements, the liquid is substantially completely vaporized.

In one embodiment of the invention, the liquid is delivered to a solenoid valve by a pump. A control circuit operates the valve such that a metered increment is supplied to a nozzle positioned in the inlet passage of the chamber. The liquid is injected into the chamber, which has been evacuated to increase the liquid's velocity. After successive impacts with the heated surfaces of the chamber, the vapor passes from the chamber via the outlet.

In another embodiment of the invention, the vaporization chamber includes a plurality of inlets and outlets. A plurality of solenoid valves supply the multicomponent liquid to a plurality of nozzles, each nozzle being positioned in one of the inlets. The liquid is delivered to the solenoid valves which are sequentially opened and closed by a control circuit. The control circuit permits a predetermined amount of liquid to pass through each nozzle before it closes one solenoid valve and opens another. The sequential opening and closing of the valves is such that the liquid to be vaporized is delivered in a steady stream. One advantage of that embodiment is that it provides for continuous vaporization of substantial quantities of a multicomponent liquid in a manner compatible with large scale sterilization techniques. This and other advantages and benefits of the present invention will become apparent from the Detailed Description Of The Preferred Embodiment hereinbelow.

BRIEF DESCRIPTION OF THE DRAWINGS

In order that the present invention may be clearly understood and readily practiced, a preferred embodiment will now be described, by way of example only, with reference to the accompanying figures wherein.

DETAILED DESCRIPTION OF THE PREFERRED EMBODIMENTS

Figure 1:
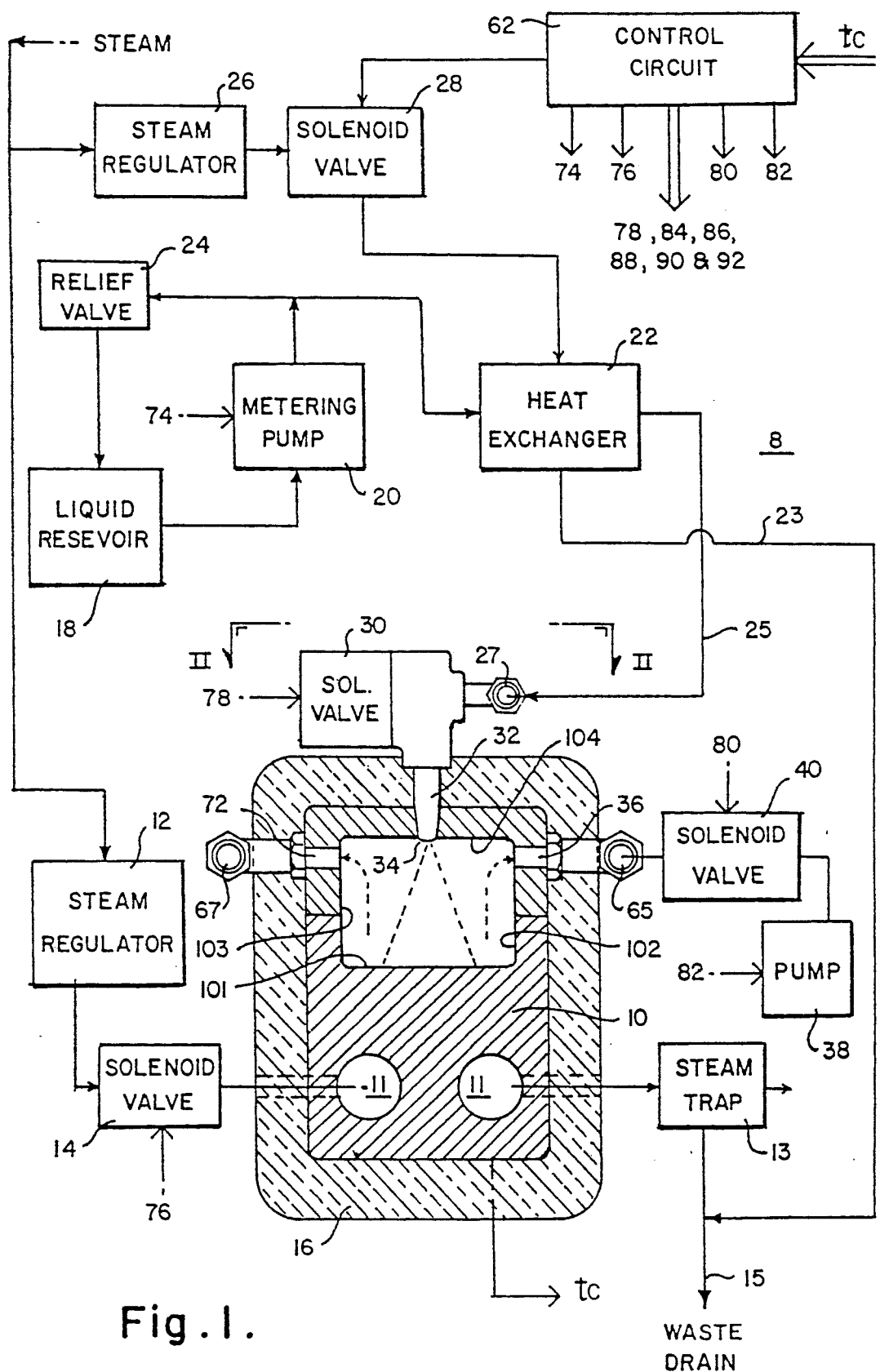
FIG. 1 is a schematic diagram of an apparatus for vaporizing a multicomponent liquid, including a cross sectional view of the vaporization chamber, constructed according to the teachings of the present invention.

In FIG. 1, a schematic diagram of an apparatus 8 capable of vaporizing large quantities of a multicomponent liquid is illustrated. A vaporization chamber 10 having several interior surfaces 101, 102, 103, and 104 is provided. A bore 11 extends therethrough. The chamber 10 may be heated to a sufficient temperature to vaporize the multicomponent liquid by passing steam through bore 11. That steam may be supplied by a steam regulator 12 and a solenoid valve 14. Solenoid valve 14 is operated by a control circuit 62 through a signal output on a control line 76. The steam exits vaporization chamber 1? by passing from bore 11 to a steam trap 13 and then through a line 15 to a waste drain for disposal.

Figure 2:
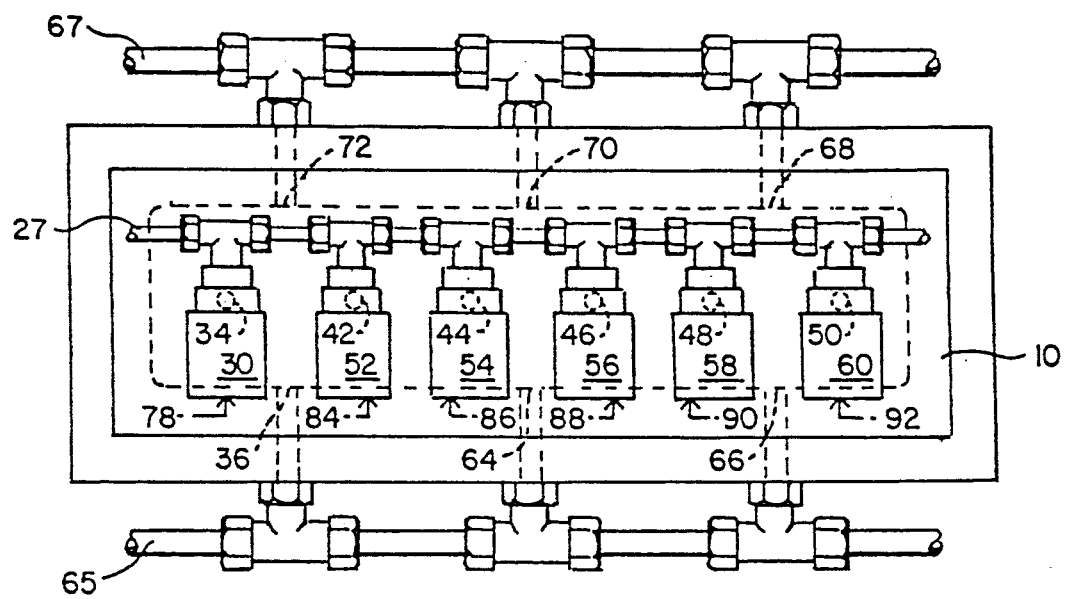
FIG. 2 is a top plan view of the vaporization chamber and manifolds illustrated in FIG. 1.
Figure 3:
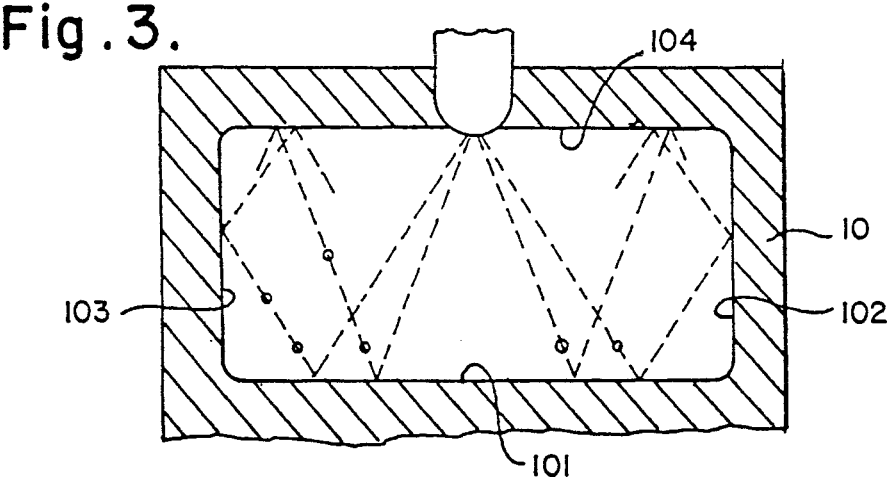
FIG. 3 is a diagram showing multiple impingement of liquid on the several surfaces of the vaporization chamber.
Figure 4:
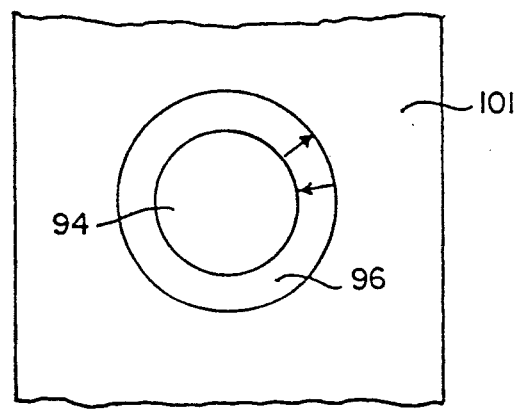
FIG. 4 shows disbursement of the liquid over the bottom surface of the chamber as a function of pressure.

Vaporization chamber 10 has a plurality of inlets 34, 42, 44, 46, 48, and 50, seen best in FIG. 2, for inputting liquid into the chamber 10 and a plurality of outlets 36, 64, 66, 68, 70, and 72 for passage of vapor from the chamber 10. The outlets 36, 64, and 66 are connected to a first output manifold 65 while the outlets 68, 70, and 72 are connected to a second output manifold 67. Each inlet 34, 42, 44, 46, 48, and 50 is provided with a nozzle, one of which 32 is shown in FIG. 1. Liquid is injected into the chamber at the desired velocity and particle size by selecting a spray nozzle of the proper design and size. For example, the nozzle may be one capable of generating particles having a mean volume diameter ranging from eighty-five microns at forty psig to sixty-five microns at one hundred psig. That is the equivalent of a misty rain.

The liquid to be injected into the chamber 10 is pumped from a reservoir 18 by a metering pump 20 to a heat exchanger 22. The metering pump 20 is operated by control circuit 62 through a signal output on a control line 74. A relief valve 24 is provided to regulate flow of excess liquid back to reservoir 18. A steam regulator 26 supplies the source of heat for heat exchanger 22. The flow of steam from regulator 26 to heat exchanger 22 is controlled by a solenoid valve 28 which is controlled by the control circuit 62. Steam exits the heat exchanger 22 to the waste drain through a line 23.

The heated liquid leaves the heat exchanger 22 through a line 25 which supplies the heated liquid to a supply manifold 27, seen best in FIG. 2. The supply manifold 27 supplies the heated liquid to a plurality of solenoid valves 30, 52, 54, 56, 58, and 60. One solenoid valve is provided for each nozzle although if nozzles will be operated in pairs, only one solenoid valve is needed for each pair.

Heated liquid is supplied with sufficient pressure so that when one of the solenoid valves 30, 52, 54, 56, 58, or 60 is opened, the liquid is injected through the nozzle associated with that valve into chamber 10 with sufficient velocity to ensure multiple impingements of the liquid with the heated surfaces 101, 102, 103, and 104 of the chamber 10. Successive impacts of the liquid with the heated surfaces increase the fraction of the liquid increment which vaporizes so that vaporization is substantially complete. Each solenoid valve 30, 52, 54, 56, 58, and 60 is operated by the control circuit 62 through a signal output on control lines 78, 84, 86, 88, 90, and 92, respectively.

The first output manifold 65 may be connected to a vacuum pump 38 through a solenoid valve 40. The vacuum pump 38 is operated by the control circuit 62 through a signal output on a control line 82 while the solenoid valve 40 is operated by a signal output on a control line 80. Pump 38 evacuates chamber 10, eliminating air resistance, so that the velocity of the injected liquid increments necessary for multiple impingements is reached. Additionally, the vacuum created by pump 38 may transport the vapor from the outlets 36, 64, 66, 68, 70, and 72 to a sterilization chamber which is not shown.

Completing the description of the apparatus 8, the heat within the chamber 10 may be conserved using any well-known form of insulation 16. When the multicomponent liquid to be vaporized is hydrogen peroxide, it is suggested that the chamber 10 be constructed of aluminum. Aluminum is highly compatible with hydrogen peroxide and is a very good thermal conductor.

In operation, the control circuit 62 sequentially opens and closes the plurality of solenoid valves 30, 52, 54, 56, 58, and 60 so that a substantially steady steam of liquid is vaporized. In FIG. 2, solenoid valves 54 and 56 may be opened first to inject metered increments of liquid through their corresponding nozzles such that the liquid first impinges the bottom surface 101 of chamber 10 as shown in FIG. 3. As the valves are initially opened, the pressure at the corresponding nozzles is low. Pressure will increase to a maximum as the valves are fully opened and then decrease as the valves close. Because spray angle is a function of pressure, the initial spray of liquid is over a small area of surface 101 (94 in FIG. 4), then increases to a maximum area 96 of surface 101, and finally returns to the small area 94.

As shown in FIG. 3, when the liquid is injected with substantial velocity, it will first impact surface 101 of chamber 10 and then bounce to impact further upon the heated surfaces 102, 103, or 104 of chamber 10. It is known that heat transfer rates in droplet impingement are quite high and as much as fifty percent of the droplet is evaporated upon impact with a heated surface. After initial impact with surface 101, substantially one-half of the liquid is vaporized. Bouncing of the residual against the surfaces 102, 103, or 104 results in substantially complete flash vaporization. The liquid is injected in such a way that residual impact is always at an angle other than ninety degrees. No liquid film is created, so boiling and vapor separation do not occur. The bottom surface 101 of the chamber 10 is level to further discourage formation of film or puddles.

Referring back to FIG. 2, vapor outlets 36, 64, 66, 68, 70, and 72 are offset from liquid inlets 34, 42, 44, 46, 48, and 50. Thus, an increment may not exit the chamber 10 without striking the heated surfaces at least twice, resulting in substantially complete vaporization.

After a predetermined amount of liquid has contacted the surfaces 101, 102, 103, and 104 of the chamber 10, those surfaces at the location contacted by liquid from valves 54 and 56 lose a substantial amount of heat. The surfaces lose heat as they vaporize the impinging liquid until eventually efficient vaporization can no longer occur. At or before that point, control circuit 62 closes valves 54 and 56 and substantially simultaneously opens solenoid valves 52 and 58.

Valves 52 and 58 remain open to inject liquid increments through their corresponding nozzles to the portion of the surfaces of the chamber adjacent thereto. Those valves will be closed by the control circuit 62 at a predetermined time when heat dissipation from the surfaces is great enough to preclude further efficient vaporization. The control circuit 62 will substantially simultaneously close solenoid valves 52 and 58 and open valves 30 and 60. Upon loss of sufficient heat by the surfaces of the chamber contacted by liquid from valves 30 and 60, the control circuit 62 will close solenoid valves 30 and 60 and reopen solenoid valves 54 and 56. That completes one pulsing cycle of the six solenoid valves. That pulsing cycle may be repeated continuously until the desired amount of vapor has been generated.

An apparatus 8 was constructed and operated according to the following sequence. The control circuit 62 opens solenoid valve 14 which is operated by the signal output on the control line 76 of control circuit 62. Valve 14 allows steam from steam regulator 12 to enter bore 11 to heat chamber 10. When chamber 10 is heated to a proper vaporization temperature of 220° F., as indicated by a temperature signal $t_c$ produced by a thermistor or the like (not shown) positioned in chamber 10, the vaporization process commences.

The pump 20, operated by the signal output on the control line 74 of the control circuit 62, supplies liquid hydrogen peroxide from the reservoir 18, through the heat exchanger 22, to the supply manifold 27 at a pressure of thirty psig. That pressure corresponds to a particle size of 100 microns. When the pump 20 is operative, the control circuit 62 opens valve 28 which allows steam to enter the heat exchanger 22 so that the hydrogen peroxide is heated to a temperature of 120° F. However, in the embodiment of the invention that was built and tested, the heat exchanger 22 was not used. The desired velocity of the liquid can be achieved with proper selection of pump pressure and spray nozzle size and design.

The control circuit 62 produces signals on control lines 86 and 88 to open solenoid valves 54 and 56. Valves 54 and 56 remain open for 310 milliseconds. All solenoid valves are then closed for 110 milliseconds. Control circuit 62 produces signals on control lines 84 and 90 to open valves 52 and 58. Valves 52 and 58 remain open for 310 milliseconds. All solenoid valves are then closed for 110 milliseconds. Control circuit 62 produces signals on control lines 78 and 92 to open valves 30 and 60. Valves 30 and 60 remain open for 310 milliseconds. All valves are then closed for 110 milliseconds. That sequence comprises one pulsing cycle. That cycle was repeated continuously for one minute, during which time 150 grams of hydrogen peroxide were vaporized. That output is sufficient to supply the quantities of vapor phase sterilant needed to establish a desired concentration in large sterilizers, rooms, glove boxes, lyophilizers, incubators, or any other large containers, even in situations where a portion of the vaporized sterilant is continually degrading.

Those of ordinary skill in the art will recognize that the function of control circuit 62 may be provided by a plurality of timers and relays or, preferably, by an appropriately programmed microprocessor. Sources of heat such as electrical resistance heaters or natural gas may be used in place of the steam heat illustrated in the figures. The apparatus 8 may be constructed to be portable so that it may be carried from location to location and connected to any suitable enclosure.

While the present invention has been described in conjunction with preferred embodiments thereof, modifications and variations will be readily apparent to those of ordinary skill in the art. This disclosure and the following claims are intended to cover all such modifications and variations.

What is claimed is:

1. An apparatus for vaporizing a multicomponent liquid, comprising:
   a vaporization chamber having a plurality of surfaces, a first inlet and a second inlet for passage of the liquid into said chamber, and an outlet for passage of vapor from said chamber;
   means for heating said surfaces of said chamber to a temperature sufficient to vaporize the liquid;
   means for injecting the liquid in metered increments into said chamber with sufficient velocity to ensure multiple impingements with said surfaces such that the liquid is substantially completely vaporized after said multiple impingements, said means for injecting comprising a first solenoid valve for supplying said metered increments to a first nozzle positioned in said first inlet and a second solenoid valve for supplying said metered increment to a second nozzle positioned in said second inlet and wherein said means for injecting includes a control circuit for sequentially opening and closing said first and said second valves such that said apparatus is capable of vaporizing a substantially steady stream of the liquid.

2. The apparatus recited in claim 1 wherein said means for injecting includes a reservoir for the liquid and a pump for supplying the liquid to said first and second solenoid valves.

3. The apparatus recited in claim 2 additionally comprising means for heating the liquid prior to injection into said vaporization chamber, said means for heating being located between said pump and said first and second solenoid valves.

4. The apparatus recited in claim 1 additionally comprising a second outlet for passage of vapor from said chamber, and wherein said first and second outlets are offset with respect to said first and second inlets such that the liquid increments are substantially completely vaporized before exiting said chamber.

5. The apparatus recited in claim 1 wherein said chamber has a bore extending therethrough, and wherein said means for heating said surfaces of said vaporization chamber includes means for supplying steam to said bore.

6. The apparatus recited in claim 1 additionally comprising means connected to said outlet for evacuating said vaporization chamber to reduce air resistance.

7. An apparatus for vaporizing a multicomponent liquid, comprising:
   a vaporization chamber having a plurality of interior surfaces, a plurality of inlets for passage of the liquid into said chamber, and a plurality of outlets for passage of vapor from said chamber;
   means for heating said surfaces of said chamber to a temperature sufficient to vaporize the liquid;
   a plurality of nozzles, each nozzle being positioned in one of said inlets;
   a plurality of solenoid valves for supplying liquid in metered increments to said plurality of nozzles;
   a pump for supplying the liquid to said plurality of solenoid valves with sufficient pressure such that when said valves are open the liquid is injected into said chamber with sufficient velocity to ensure multiple impingements with said surfaces whereby the liquid is substantially completely vaporized after said multiple impingements; and
   a control circuit for sequentially opening and closing said plurality of valves such that said apparatus is capable of vaporizing a substantially steady stream of the liquid.

8. The apparatus recited in claim 7 wherein said chamber has a bore extending therethrough, and said means for heating said surfaces of said vaporization chamber includes means for supplying steam to said bore.

9. The apparatus recited in claim 7 additionally comprising a heat exchanger for heating the liquid prior to injection into said vaporization chamber, said heat exchanger being located between said pump and said plurality of solenoid valves.

10. A method of vaporizing a multicomponent liquid, comprising the steps of:

heating the interior surfaces of a vaporization chamber to a temperature sufficient to vaporize the liquid, said chamber having at least two inlets for inputting the liquid into said chamber and an outlet for outputting of vapor from said chamber;

injecting the liquid into said chamber through said inlets in alternating fashion between different areas of said chambers with sufficient velocity to ensure multiple impingements with said different areas of said surfaces such that the liquid is substantially completely vaporized after said multiple impingements; and outputting the vapor from said chamber through said outlet.

11. The method recited in claim 10 additionally comprising the step of heating the liquid prior to injecting the liquid into the chamber.

12. The method recited in claim 10 wherein the step of injecting the liquid into said chamber includes injecting the liquid into the chamber in metered increments.

13. The method recited in claim 12 wherein the step of injecting metered increments of the liquid into said chamber includes the step of operating a plurality of valves such that the metered increments are injected into said chamber substantially continuously.

14. An apparatus for vaporizing a multicomponent liquid, comprising:

a vaporization chamber having a plurality of surfaces, at least two inlets for passage of the liquid into said chamber, and an outlet for passage of vapor from said chamber;

means for heating said surfaces of said chamber to a temperature sufficient to vaporize the liquid;

at least two valves, each said valve being operatively connected to one said inlet for injecting the liquid through said inlets into said chamber with sufficient velocity to ensure multiple impingements with said surfaces such that the liquid is substantially completely vaporized after said multiple impingements;

control means for opening and closing said valves; and means for removing air from said chamber through said outlet.

15. An apparatus for vaporizing a multicomponent liquid, comprising:

a vaporization chamber having a plurality of interior surfaces, a plurality of outlets for passage of the liquid into said chamber, and a plurality of outlets for passage of vapor from said chamber;

means for heating said surfaces of said chamber to a temperature sufficient to vaporize the liquid;

a plurality of nozzles, each nozzle being positioned in one of said inlets;

a plurality of solenoid valves for supplying liquid in metered increments to said plurality of nozzles;

a pump for supplying the liquid to said plurality of solenoid valves with sufficient pressure such that when said valves are open the liquid is injected into said chamber with sufficient velocity to ensure multiple impingements with said surfaces whereby the liquid is substantially completely vaporized after said multiple impingements; and a control circuit for sequentially opening and closing said plurality of valves such that said apparatus is capable of vaporizing a substantially steady stream of the liquid.

16. A method of vaporizing a multicomponent liquid, comprising the steps of:

removing air from a vaporization chamber;

heating interior surfaces of said vaporization chamber to a temperature sufficient to vaporize the liquid said chamber having at least two inlets for inputting the liquid into said chamber arranged so that each inlet directs the liquid to a different predetermined area of said surfaces of said chamber and an outlet for outputting of vapor from said chamber;

alternately injecting the liquid into said chamber through one of said inlets and then through the other of said inlets so that liquid is directed in an alternating fashion between said different predetermined areas of said surfaces with sufficient velocity to ensure multiple impingements of said liquid with said surfaces such that the liquid is substantially completely vaporized after said multiple impingements; and outputting the vapor from said chamber through said outlet.

* * * * *

UNITED STATES PATENT AND TRADEMARK OFFICE
CERTIFICATE OF CORRECTION

PATENT NO. : 5,068,087
DATED : November 26, 1991
INVENTOR(S) : Robert W. Childers It is certified that error appears in the above-identified patent and that said Letters Patent is hereby corrected as shown below:

Col. 1, line 60, delete "beat" and substitute --heat-- therefor.

Col. 3, line 4, delete "1?" and substitute --10-- therefor.

Col. 8, line 6, delete "outlets" and substitute --inlets-- therefor.

Col. 8, line 8, after "chambers;" add --means for evacuating said vaporization chamber to reduce air resistance;--

Col. 8, line 30, after "liquid", insert a --,--.

Signed and Sealed this

Thirteenth Day of April, 1993

*Attest:*

STEPHEN G. KUNIN

*Attesting Officer*      *Acting Commissioner of Patents and Trademarks*